(12) United States Patent
Turtzo

(10) Patent No.: US 6,699,209 B2
(45) Date of Patent: Mar. 2, 2004

(54) FOOT SPLINT FOR TREATMENT OF PLANTAR FASCIITIS

(75) Inventor: Craig H. Turtzo, Tampa, FL (US)

(73) Assignee: MedAssist-OP, Inc., Tampa, FL (US)

( * ) Notice: Subject to any disclaimer, the term of this patent is extended or adjusted under 35 U.S.C. 154(b) by 0 days.

(21) Appl. No.: 09/875,357

(22) Filed: Jun. 6, 2001

(65) Prior Publication Data
US 2002/0188239 A1 Dec. 12, 2002

(51) Int. Cl.[7] ................................................. A61F 5/00
(52) U.S. Cl. ........................... 602/27; 602/5; 602/23
(58) Field of Search ............................ 602/6–8, 16, 23, 602/26–29, 5, 12, 30; 264/222, 223

(56) References Cited

U.S. PATENT DOCUMENTS

| 4,241,523 A | * 12/1980 | Daswick ........................ 36/30 R |
| 4,351,324 A | * 9/1982 | Bronkhorst |
| 4,771,768 A | 9/1988 | Crispin |
| 4,962,760 A | 10/1990 | Jones |
| 5,176,623 A | * 1/1993 | Stetman et al. ................ 602/27 |
| 5,269,748 A | * 12/1993 | Lonardo ........................ 602/27 |
| 5,507,106 A | * 4/1996 | Fox ................................ 36/103 |
| 5,542,912 A | 8/1996 | Hess |
| 5,569,173 A | 10/1996 | Varn |
| 5,595,003 A | * 1/1997 | Snow ............................... 36/28 |
| 5,799,659 A | 9/1998 | Stano |
| 5,865,779 A | 2/1999 | Gleason |
| 5,887,591 A | * 3/1999 | Powell et al. |
| 5,921,243 A | 7/1999 | Shakoor |
| 5,944,679 A | * 8/1999 | DeToro ......................... 602/27 |

OTHER PUBLICATIONS

Foot & Ankle International: Effective Treatment of Chronic Plantar Fasciitis with Dorsiflexion Night Splints: A Crossover Prospective Randomized Outcome Study, Powell et al., Foot & Ankle International/vol. 19, No. 1/Jan. 1998.

Effective Treatment of Chronic Plantar Fasciitis with Dorsiflexion Night Splints: A Crossover Prospective Randomized Outcome Study.

* cited by examiner

Primary Examiner—Nicholas D. Lucchesi
Assistant Examiner—Lalita M. Hamilton
(74) Attorney, Agent, or Firm—Greensfelder, Hemker & Gale

(57) ABSTRACT

A foot splint for securing a heel and toes of the foot in an extended position comprising an elongated rigid plate including an elevated proximal region and an elevated distal region and an upper surface and a lower surface. At least one elongated member extends from the periphery of the plate for securing a mid-portion of the foot to the upper surface such that the elevated distal region elevates the toes and elevated proximal region elevates the heel of the foot for stretching the plantar fascia of the foot.

18 Claims, 4 Drawing Sheets

FOOT SPLINT FOR TREATMENT OF PLANTAR FASCIITIS

BACKGROUND OF THE INVENTION

1. Field of the Invention

The present invention relates to a splint, and more particularly to a foot splint. More specifically, the present invention relates to a foot splint for treatment of plantar fasciitis.

2. Prior Art

There are many conditions in which it may be desirable to secure a patient's foot in an extended position. For example, after surgery braces or splints may be provided to a patient unable to ambulate. The splint secures the foot at approximately a ninety degree angle with respect to the leg in order to avoid a condition known as "drop foot". However, a more common condition that afflicts many patients is plantar fasciitis. Plantar fasciitis occurs when the plantar fascia, a fibrous membrane disposed longitudinally across the bottom of the foot, becomes irritated. This irritation may be caused by standing for extended periods of time. Generally, plantar fasciitis manifests itself in the form of heel pain. Its effects are most pronounced with the first steps taken for the day as a result of plantar flexion of the plantar fascia during the night.

Plantar fasciitis has been traditionally treated in a number of ways including non-steroidal anti-inflammatory medicines, cortisone injections, shoe modifications, physical therapy, and even surgery. Additionally, it has been found that the painful effects of plantar fasciitis may be treated by dorsiflexing the foot. Dorsiflexion refers to extending the bottom of the foot such that an angle of less than ninety degrees is formed with the lower leg using a dorsiflexion device. Such dorsiflexion devices are worn by the patient overnight which provides relief from the painful effects of plantar fasciitis. The results of a clinical study authored by Powell, M. D., et al., entitled *Effective Treatment of Chronic Plantar Fasciitis with Dorsiflexion Night Splints: A Crossover Prospective Randomized Outcome Study*, which appeared in *Foot & Ankle International/Vol.* 19, No. 1/January 1998, revealed an eighty eight percent improvement rate for control group subjects treated solely by wearing dorsiflexion night splints for a period of one month. Moreover, it has been found that a patient may receive benefits from wearing a splint which maintains only the toes in a dorsiflexed position with respect to the foot, without having to dorsiflex the entire foot with respect to the leg. By not having to dorsiflex the entire foot, the splint is much more comfortable for a patient to wear.

U.S. Pat. Nos. 5,799,659 and 5,887,591 to Stano and Powell et al. ("Powell") collectively disclose a restraint including a single wedge disposed between a user's foot and a foot plate. The wedge in the Powell reference elevates the user's toes with respect to the foot plate, while the wedge in the Stano reference extends the entire length of the user's foot. While the Powell reference provides an amount of dorsiflexion of the toes, both references totally lack an elevated heel portion and inventive three-point support system contained in the present invention which will be discussed in more detail below. Additionally, both the Powell and Stano restraints contain the disadvantage of a rigid upper leg portion that is fixedly attached to the user's leg which is cumbersome and uncomfortable for the user to wear.

U.S. Pat. No. 4,962,760 to Jones discloses an orthopedic restraint apparatus having an adjustable ankle articulation system and a foot portion having a hingedly mounted toe member which permits intermittent dorsiflexion of the toes. While the Jones reference discloses features which permit more comfortable patient ambulation, it is cumbersome to wear. Additionally, the Jones device provides for only a limited range of ankle articulation which may be uncomfortable for a patient to wear for an extended period of time, especially when worn overnight.

An additional advancement in the art is found in U.S. Pat. No. 4,351,324 to Bronkhorst which discloses a walking device that is strapped to the user's leg having a raised heel portion and a raised toe support. By being strapped to the user's leg at a fixed ninety degree angle, the foot is maintained in a dorsiflexed position. However, the purpose of the Bronkhorst device is to prevent a user from ambulating on the ball of the foot, and may not provide sufficient dorsiflexion of the toes. Moreover, because the Bronkhorst device maintains the user's foot at a fixed ninety degree angle with respect to the leg, it may be uncomfortable for a patient to wear overnight. Accordingly, some users have refused or are unable to wear this device, thereby limiting its utility in this application.

Therefore, there appears a need in the art for a foot splint for treatment of plantar fasciitis which overcomes the disadvantages of the prior art.

OBJECTS AND SUMMARY OF THE INVENTION

The primary object of the present invention is to provide a foot splint for treatment of plantar fasciitis.

Another object of the present invention is to provide a foot splint for treatment of plantar fasciitis that permits ease of ambulation by the user.

A further object of the present invention is to provide a foot splint for treatment of plantar fasciitis that may be comfortably worn for extended periods of time by a patient, namely overnight while the patient sleeps.

Another further object of the present invention is to provide a foot splint for treatment of plantar fasciitis that is of compact construction.

Yet another object of the present invention is to provide a foot splint for treatment of plantar fasciitis that permits unrestricted ankle movement.

Yet another further object of the present invention is to provide a foot splint for treatment of plantar fasciitis that is inexpensive to manufacture.

These and other objects of the present invention are realized in the preferred embodiment of the present invention, described by way of example and not by way of limitation, which provides for a foot splint for treatment of plantar fasciitis.

In brief summary, the present invention overcomes and substantially alleviates the deficiencies in the prior art by providing a foot splint comprising an elongated rigid plate having an elevated proximal region and an elevated distal region. Additionally, the plate further has an upper surface and a lower surface and a securing means extending from the periphery of the plate. In application, the securing means secures a mid-portion of a patient's foot to the upper surface such that the elevated distal region elevates the toes and the elevated proximal region elevates a heel of the foot for stretching the plantar fascia of the foot.

Additional objects, advantages and novel features of the invention will be set forth in the description which follows, and will become apparent to those skilled in the art upon examination of the following more detailed description and drawings in which like elements of the invention are similarly numbered throughout.

DETAILED DESCRIPTION OF THE INVENTION

Figure 1:
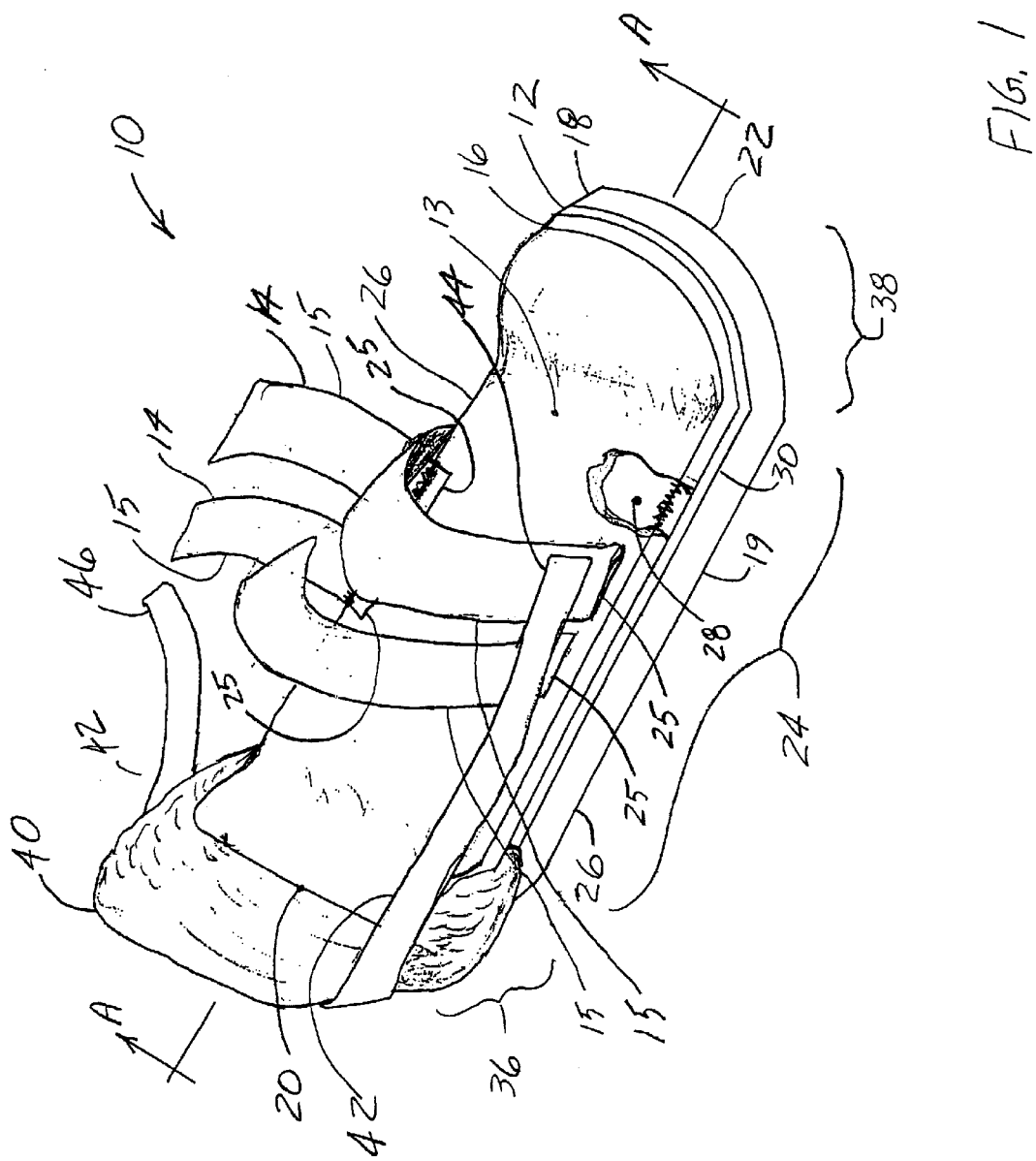
FIG. 1 is a perspective view of a foot splint according to the present invention.
Figure 4:
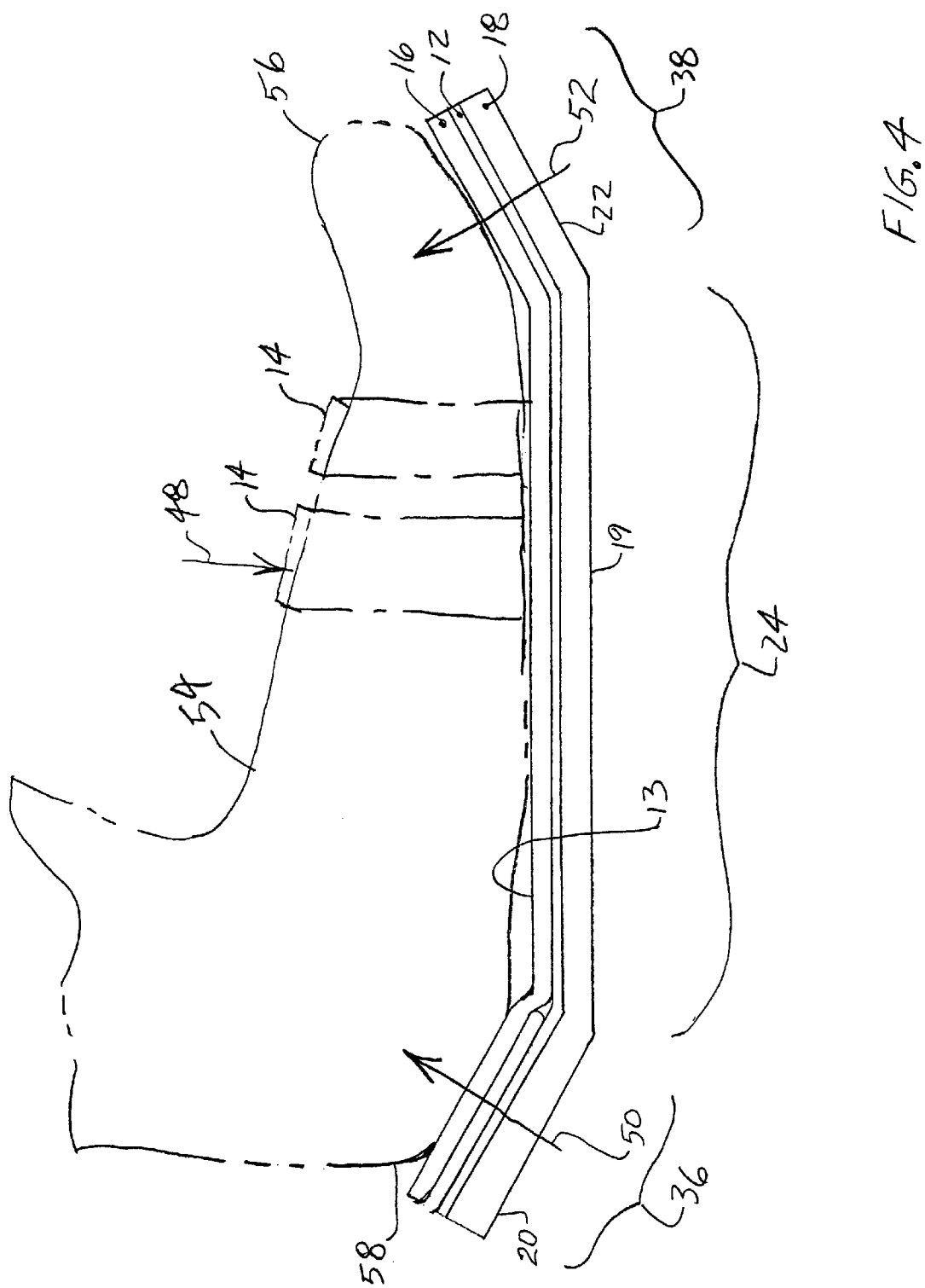
FIG. 4 is a simplified side view of loading forces applied to a foot by the foot splint according to the present invention.

Referring to the drawings, the preferred embodiment of the foot splint of the present invention is illustrated and generally indicated as 10 in FIG. 1. Foot splint 10 comprises a rigid plate 12 for support, a securing means 14 attached to plate 12 for securing a patient's foot to splint 10, a resilient first layer 16 for providing cushioning, and a resilient second layer 18 having a lower surface 19 which provides additional cushioning. Referring to FIGS. 1 and 4, plate 12 is interposed between first layer 16 and second layer 18 having an elevated proximal region 36 and an elevated distal region 38 for supporting a foot 54 in an extended position and for dorsiflexing toes 56. As further shown, securing means 14 extends from along the periphery of plate 12 for securing foot 54 in its extended position.

Figure 2:
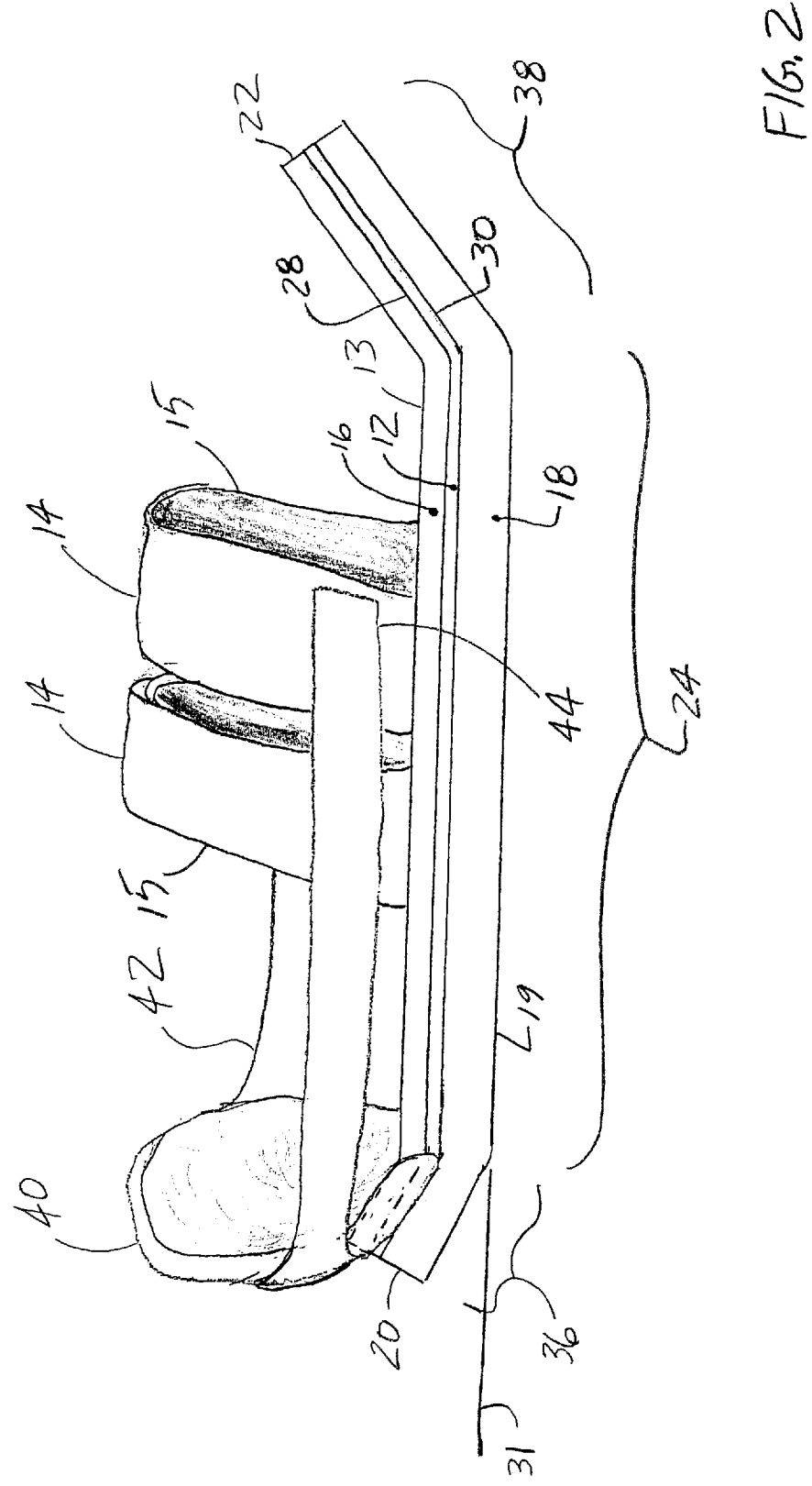
FIG. 2 is a side view of the foot splint according to the present invention.
Figure 3:
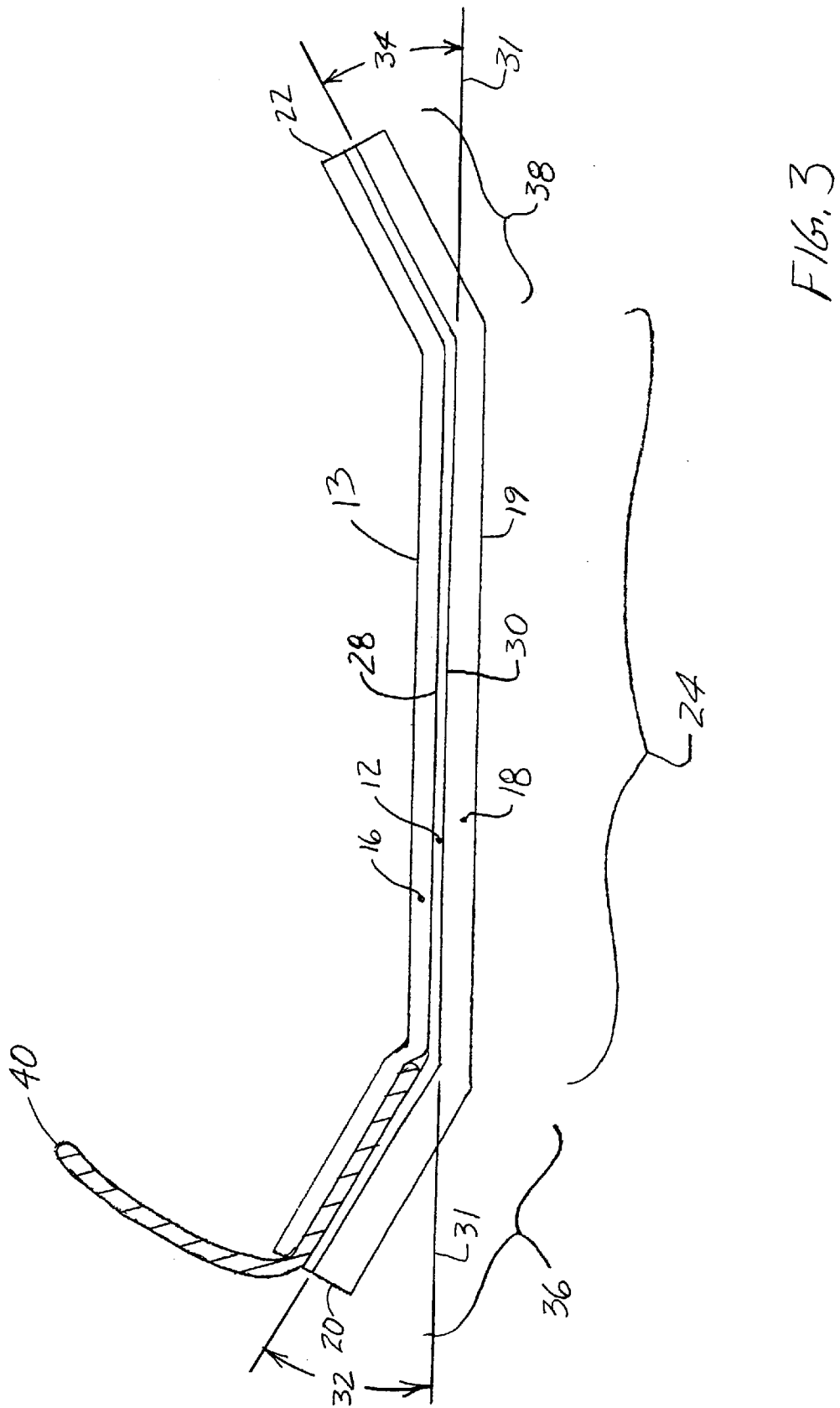
FIG. 3 is a sectional view of the foot splint taken along line A—A of FIG. 1 according to the present invention.

Referring to FIGS. 1–4, rigid plate 12 has a proximal end 20 and a distal end 22 with a flat portion 24 formed therebetween which defines a reference plane 31. Plate 12 further comprises an upper surface 28 and a lower surface 30 bounded by a lateral portion 26. Extending along proximal end 20 is an elongated proximal region 36 which is defined by a proximal angle 32 that extends above reference plane 31 for securing a patient's heel 58 (FIG. 4). Preferably, proximal angle 32 is in a range of between 20 and 40 degrees with a 30 degree angle being the most preferred angle. Referring specifically to FIGS. 3 and 4, extending along distal end portion 22 is an elevated distal region 38 that is defined by distal angle 34 which extends above reference plane 31 for securing a user's toes 56. Preferably distal angle 34 is in a range of between 20 and 40 degrees with a 30 degree angle being the most preferred angle. As further shown, flat portion 24 supports a portion of a patient's foot 54 between toes 56 and heel 58 along a flat plane. Formed adjacent lateral portion 26 are longitudinal slots 25 for receiving securing means 14 as shall be discussed in greater detail below.

Another aspect of the present invention is that the resilient first layer 16 includes an upper surface 13 disposed atop upper surface 28 of plate 12 for providing cushioning and added patient comfort. As is particularly shown in FIG. 4, upper surface 13 is sized and shaped to comfortably receive foot 54. Referring to FIGS. 1 and 3, a retaining portion 40 is interposed between plate 12 and first layer 16 along elevated proximal region 36. One skilled in the art can appreciate that longitudinal slots 25 are also formed in-line with those formed in plate 12 to receive securing means 14.

Referring to FIGS. 1 and 3, resilient second layer 18 is disposed beneath lower surface 30 of plate 12 for providing additional comfort to the patient. Moreover, lower surface 19 of second layer 18 provides a reliable gripping surface for foot splint 10 while the user ambulates.

Referring to FIGS. 1, 2 and 4, securing means 14 comprises a pair of elongated members 15 for securing foot 54 to foot splint 10. In assembly, each member 15 is passed through a respective slot 25 adjacent lateral portion 26 by proceeding through first layer 16 and plate 12. Each member 15 is then forced in a transverse direction between lower surface 30 and second layer 18 toward its corresponding slot 25. Finally, once each member 15 is secured to its corresponding slot 25 formed adjacent the opposing side of lateral portion 26, each member 15 is then passed through lower surface of plate 12 such that members 15 extend outwardly through upper surface 13 of first layer 16. It should be appreciated by one skilled in the art that elongated members 15 can pass through and beneath plate 12 for added patient comfort. To secure foot 54, opposing ends of members 15 are wrapped around foot 54 and attached to one another, preferably with VELCRO®, for ease of assembly and disassembly, although any suitable type of fastener, such as mechanical fasteners, buckles, adhesives or the like may be used.

As illustrated in FIG. 4, securing means 14 imposes a retaining force 48 on foot 54 which generates resulting first and second reactive forces 50,52 along elevated proximal region 36 and elevated distal region 38, respectively, to define a three point pressure system. The three point pressure system provides proper extension to the plantar fascia of foot 54 without restricting ankle movement when foot splint 10 is properly worn.

Referring to FIGS. 1–4, retaining portion 40 is interposed between plate 12 and first layer 16 and extends from elevated proximal region 36 of foot splint 10. Preferably, retaining portion 40 includes an adjustable strap 42 having a proximal end 44 securely attached to a side of securing means 14 and a distal end 46 for selective adjustable attachment with an opposing side of securing means 14. By securing retaining portion 40 to foot 54 after attaching securing means 14 about foot 54, one skilled in the art can appreciate that foot 54 is effectively captured by foot splint 10.

The operation of foot splint 10 shall now be discussed. With securing means 14 and retaining portion 40 in open positions, the patient's foot 54 is placed in conformal contact with upper surface 13. By establishing such conformal contact, the patient's toes 56 are placed in a dorsiflexed position by upper surface 13 along elevated distal region 38, and the patient's heel 58 is raised along elevated proximal region 36. By dorsiflexing the patient's toes 56, the patient's plantar fascia is thereby stretched. As further shown, upon attaching securing means 14 about foot 54 and attaching retaining portion 40 to securing means 14, a three point pressure system is established that provides maximum stretch to the patient's plantar fascia which permits the patient to receive the maximum therapeutic benefits of foot splint 10.

It should be appreciated by one skilled in the art that securing means 14 may be configured to extend from the periphery of foot splint 10 without the requirement that securing means completely wrap around a foot. In other words, by applying an adhesive, or other bonding material or mechanical device along lateral portion 26, one end of securing means 14 may be attached thereto, with the other end of securing means 14 passing over foot 54 and attaching to the opposing side of lateral portion 26. Additionally, securing means 14 may further extend transversely through longitudinal slot 25 and pass beneath first layer 16. In the alternative, securing means 14 may proceed beneath lower surface 19 of second layer 18 before passing around foot 54.

It should be understood from the foregoing that, while particular embodiments of the invention have been illustrated and described, various modifications can be made thereto without departing from the spirit and scope of the present invention. Therefore, it is not intended that the invention be limited by the specification; instead, the scope of the present invention is intended to be limited only by the appended claims.

I claim:

1. A foot splint for simultaneously securing and applying pressure to a heel and toes of the foot in a predetermined position comprising:

an elongated rigid plate defining a plane having an elevated proximal region defined by forming an angle on one end of said plate above said plane thereof, and an elevated distal region defined by forming an angle on the other end of said plate above said plane thereof, said plate further having an upper surface and a lower surface;

at least one elongated member extending from the periphery of said plate;

wherein said at least one elongated member secures a mid-portion of the foot to said upper surface such that said elevated distal region elevates the toes relative to said mid-portion of the foot, and said elevated proximal region elevates the heel relative to said mid-portion of the foot for stretching the plantar fascia of the foot.

2. The foot splint according to claim 1 wherein said at least one elongated member, said elevated proximal region and said elevated distal region define a three point pressure system which dorsiflexes the foot.

3. The foot splint according to claim 1 wherein said angles for defining an elevated proximal and distal region are in a range of between 20 and 40 degrees.

4. The foot splint according to claim 1 wherein said angles for defining an elevated proximal and distal region are 30 degrees.

5. The foot splint according to claim 1 wherein said foot splint further comprises a first layer of resilient material formed adjacent said upper surface of said plate.

6. The foot splint according to claim 1 wherein the foot splint further comprises a second layer of resilient material formed adjacent said lower surface of said plate.

7. The foot splint according to claim 1 wherein said second layer provides a reliable gripping surface with a walking surface for patient ambulation.

8. The foot splint according to claim 1 wherein said plate has a lateral, portion between said proximal and distal regions; said at least one elongated member extending from said lateral portion in a transverse direction to secure said mid-portion of the foot to said plate.

9. The foot splint according to claim 1 wherein said at least one elongated member further includes a retaining portion extending from said proximal region of said plate to secure the foot in said foot splint.

10. The foot splint according to claim 9 wherein said retaining portion is adjustably attached to said at least one elongated member.

11. A foot splint for simultaneously securing and applying pressure to a heel and toes of the foot in a predetermined position comprising:

an elongated rigid plate defining a longitudinal plane, said plate further having an elevated proximal region defined by forming an angle on one end of said plate above said plane thereof, and an elevated distal region defined by forming an angle on the other end of said plate above said plane thereof, said plate further having an upper surface and a lower surface;

at least one elongated member extending from the periphery of said plate;

wherein said at least one elongated member secures a mid-portion of the foot to said upper surface such that said elevated distal region elevates the toes relative to said mid-portion of the foot, and said elevated proximal region elevates the heel relative to said mid-portion of the foot for dorsiflexing the foot.

12. The foot splint according to claim 11 wherein said middle portion of said plate is flat.

13. A foot splint for simultaneously securing and applying pressure to a heel and toes of the foot in a predetermined position comprising:

an elongated rigid plate having an elevated proximal region defined by forming an angle on one end of said plate above said plane thereof, and an elevated distal region defined by forming an angle on the other end of said plate above said plane thereof, said plate further having an upper surface and a lower surface;

a securing means extending from the periphery of said plate; wherein said securing means secures a mid-portion of said foot to said upper surface such that said elevated distal region elevates the toes relative to said mid-portion of the foot and elevated proximal region elevates the heel relative to said mid-portion of the foot for stretching the plantar fascia of the foot, wherein said securing means, said elevated distal region and said elevated proximal region define a three point pressure system.

14. A foot splint for simultaneously securing and applying pressure to a heel and toes of the foot in a predetermined position comprising:

an elongated rigid plate defining a longitudinal plane, said plate bounded by opposing lateral portions, said plate further having an elevated proximal region defined by forming an angle on one end of said plate above said plane thereof, and an elevated distal region defined by forming an angle on the other end of said plate above said plane thereof, said plate further having an upper surface and a lower surface;

at least one elongated member extending from the periphery of said plate;

wherein said at least one elongated member secures a mid-portion of the foot to said upper surface such that said elevated distal region elevates the toes relative to said mid-portion of the foot, and said elevated proximal region elevates the heel relative to said mid-portion of the foot for stretching the plantar fascia of the foot.

15. A method for simultaneously securing and applying pressure to a heel and toes of the foot in a predetermined position the steps of the method comprising:

a) providing a foot splint having an elongated rigid plate having an elevated proximal region defined by forming an angle on one end of said plate above said plane thereof, and an elevated distal region defined by forming an angle on the other end of said plate above said plane thereof, said plate further including an upper surface and a lower surface; at least one elongated member extending from the periphery of said plate; wherein said at least one elongated member secures a mid-portion of the foot to said upper surface such that said elevated distal region elevates the toes relative to said mid-portion of the foot, while said elevated proximal region elevates the heel relative to said mid-portion of the foot for stretching the plantar fascia of the foot;

b) ensuring said at least one elongated member is in an open position;

c) placing the foot in conformal contact with said upper surface of the plate; and d) attaching said at least one elongated member a out the foot.

16. The method according to claim 15 wherein said step a) further comprises a retaining portion extending from said proximal region to secure the foot in said splint.

17. The method according to claim 16 wherein said step b) further includes ensuring said retaining portion is in an open position for accepting the foot.

18. The method according to claim 17 wherein said step d) further includes attaching said retaining portion to said at least one elongated member.

* * * * *